US010767973B2

(12) United States Patent
Wang et al.

(10) Patent No.: US 10,767,973 B2
(45) Date of Patent: Sep. 8, 2020

(54) DUAL-EDGE SAMPLING WITH K-CLOCK TO AVOID ALIASING IN OPTICAL COHERENCE TOMOGRAPHY

(71) Applicant: Alcon Inc., Fribourg (CH)

(72) Inventors: Bing Wang, Laguna Niguel, CA (US); Muhammad K. Al-Qaisi, Ladera Ranch, CA (US); Hugang Ren, Cypress, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/173,146

(22) Filed: Oct. 29, 2018

(65) Prior Publication Data

US 2019/0128659 A1 May 2, 2019

Related U.S. Application Data

(60) Provisional application No. 62/580,825, filed on Nov. 2, 2017.

(51) Int. Cl.

*G01B 9/02* (2006.01)
*A61B 3/10* (2006.01)
*A61B 5/00* (2006.01)

(52) U.S. Cl.

CPC .......... *G01B 9/02084* (2013.01); *A61B 3/102* (2013.01); *A61B 5/0066* (2013.01); *A61B 5/7257* (2013.01); *G01B 9/02004* (2013.01); *G01B 9/02091* (2013.01); *A61B 5/725* (2013.01)

(58) Field of Classification Search

CPC ........... G01B 9/02084; G01B 9/02004; G01B 9/02091; A61B 3/102; A61B 5/0066; A61B 5/7257

See application file for complete search history.

(56) References Cited

U.S. PATENT DOCUMENTS

2014/0028997 A1* 1/2014 Cable ................ G01B 9/02091 356/51
2014/0340689 A1* 11/2014 Namati ............. G01B 9/02091 356/479
2015/0300806 A1 10/2015 Goldberg et al.
2017/0065169 A1* 3/2017 Fukasawa ............. A61B 3/102

* cited by examiner

*Primary Examiner* — Dominic J Bologna

(57) ABSTRACT

Techniques and apparatus for producing sampled Optical Coherence Tomography (OCT) interference signals without aliasing, based on a swept-source OCT interference signal. An example apparatus comprises a k-clock circuit configured to selectively output a k-clock signal at any of a plurality of k-clock frequencies ranging from a minimum k-clock frequency to a maximum k-clock frequency, and an anti-aliasing filter configured to filter a swept-source OCT interference signal, to produce a filtered OCT interference signal, where the anti-aliasing filter has a cut-off frequency greater than one-half the minimum k-clock frequency but less than the minimum k-clock frequency. The apparatus further comprises an analog-to-digital (A/D) converter circuit configured to sample the filtered OCT interference signal at twice the k-clock frequency, to produce a sampled OCT interference signal. In some embodiments, the A/D converter circuit samples the filtered OCT interference signal at both rising and falling edges of the k-clock signal.

7 Claims, 3 Drawing Sheets

DUAL-EDGE SAMPLING WITH K-CLOCK TO AVOID ALIASING IN OPTICAL COHERENCE TOMOGRAPHY

TECHNICAL FIELD

Embodiments disclosed herein are related to devices, systems, and methods for providing sampled Optical Coherence Tomography (OCT) interference signals for OCT imagery.

BACKGROUND

Current ophthalmic refractive surgical methods, such as cataract surgery, intra-corneal inlays, laser-assisted in situ keratomileusis (LASIK), and photorefractive keratectomy (PRK), rely on ocular biometry data to prescribe the best refractive correction. Historically, ophthalmic surgical procedures used ultrasonic biometry instruments to image portions of the eye. In some cases, these biometric instruments generated a so-called A-scan of the eye: an acoustic echo signal from all interfaces along an imaging axis that was typically aligned with an optical axis of the eye: either parallel with it, or making only a small angle. Other instruments generated a so-called B-scan, essentially assembling a collection of A-scans, taken successively as a head or tip of the biometry instrument was scanned along a scanning line. This scanning line was typically lateral to the optical axis of the eye. These ultrasonic A- or B-scans were then used to measure and determine biometry data, such as an ocular axial length, an anterior depth of the eye, or the radii of corneal curvature.

In some surgical procedures, a second, separate keratometer was used to measure refractive properties and data of the cornea. The ultrasonic measurements and the refractive data were then combined in a semi-empirical formula to calculate the characteristics of the optimal intra-ocular lens (IOL) to be prescribed and inserted during the subsequent cataract surgery.

More recently, ultrasonic biometry devices have been rapidly giving way to optical imaging and biometry instruments that are built on the principle of Optical Coherence Tomography (OCT). OCT is a technique that enables micron-scale, high-resolution, cross-sectional imaging of the human retina, cornea, or cataract. Optical waves are reflected from an object or sample and a computer produces images of cross sections or three-dimensional volume renderings of the sample by using information on how the waves are changed upon reflection.

OCT may be performed based on time-domain processing of Fourier-domain processing. The latter approach includes a technique known as swept-source OCT, where the spectral components of the optical signal used to illuminate the sample are encoded in time. In other words, the optical source is swept (or stepped) across an optical bandwidth, with the interference signal produced by the combination of the source signal and the reflected signal being sampled at several points across this optical bandwidth. The sampling clock, which is typically designed to sample the interference signal at equally spaced points across the optical bandwidth, is referred to as a "k-clock," and the resulting samples, which are samples in the optical frequency domain or "k-space," are referred to as "k-space" samples.

In practice, the optical source is successively directed to each of a series of points on the surface of the object (e.g., the eye) being imaged, with k-space samples across the spectral bandwidth being collected at each of these points.

The k-space samples corresponding to each point are processed, using well-known digital signal processing techniques, to provide image data corresponding to a range of depths in the imaged object, i.e., an "A-scan." The A-scans across the series of points are compiled to create a B-scan; multiple B-scans, corresponding to sequential "rows" along the imaged object can be compiled to form three-dimensional image data. It will be appreciated that because of the Fourier-domain processing used in swept-source OCT, z-axis scanning, where the length of the reference arm of the interference is successively changed to obtain information at different depths in the imaged object, is not needed. Rather, depth information is obtained from the processing of the k-space samples, over a range of depths that corresponds inversely to the size of the spectral frequency increments for the k-space samples.

OCT technology is now commonly used in clinical practice, with such OCT instruments are now used in 80-90% of all IOL prescription cases. Among other reasons, their success is due to the non-contact nature of the imaging and to the higher precision than that of the ultrasound biometers.

Even with these recent advances, however, substantial further growth and development is needed for the functionalities and performance of biometric and imaging instruments.

SUMMARY

Disclosed herein are embodiments of an Optical Coherence Tomography (OCT) data acquisition and processing circuit for use in producing an OCT image based on a swept-source OCT interference signal. In various embodiments, the OCT data acquisition and processing circuit comprises a k-clock circuit configured to selectively output a k-clock signal at any of a plurality of k-clock frequencies ranging from a minimum k-clock frequency to a maximum k-clock frequency, as well as an anti-aliasing filter configured to filter the swept-source OCT interference signal, to produce a filtered OCT interference signal. The anti-aliasing filter has a cut-off frequency greater than one-half the minimum k-clock frequency but less than the minimum k-clock frequency. The OCT data acquisition and processing circuit still further includes an analog-to-digital (A/D) converter circuit coupled configured to sample the filtered OCT interference signal at twice the k-clock frequency, to produce a sampled OCT interference signal.

In some embodiments, the A/D converter circuit is configured to sample the filtered OCT interference signal on every rising edge and every falling edge of the k-clock signal. In other embodiments, the A/D converter circuit comprises first and second A/D converters, the first A/D converter being configured to sample the filtered OCT interference signal at the k-clock frequency, using the k-clock signal, and the second A/D converter being configured to separately sample the filtered OCT interference signal at the k-clock frequency, using a phase-shifted replica of the k-clock signal. In these latter embodiments, the A/D converter circuit further comprises a multiplexer to combine the sampled outputs from the first and second A/D converters to obtain the sampled OCT interference signal.

In some embodiments, the OCT data acquisition and processing circuit further comprises a swept optical source and an interferometer coupled to an output of the swept optical source, the interferometer in turn comprising a detector circuit configured to generate the swept-source OCT interference signal from an optical interference signal produced by the interferometer. In some embodiments, the OCT data acquisition and processing circuit further comprises a digital signal processing circuit configured to process the sampled OCT interference signal to obtain an OCT image, and a display configured to display the OCT image.

The embodiments described herein may be used to provide and/or operate an all-in-one device to achieve optimized OCT performance for each of several different application modes. Other advantages and variations of the above-summarized embodiments are described below.

DETAILED DESCRIPTION

In the following description, specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Embodiments of the presently disclosed techniques and apparatus may be employed in both microscope-mounted and microscope-integrated Optical Coherence Tomography (OCT) systems.

In ophthalmic applications, low-coherence interferometry techniques, like OCT, are used to provide information about spacing of eye layers. Ophthalmic biometry requires measuring anatomical and optical parameters from the anterior segment of the eye, as well as measurements performed on the full-eye length. However, measuring the full length of the eye requires certain performance tradeoffs, relative to performing anterior segment measurements, which require a shorter depth of measurement.

Several methods have been demonstrated to allow an OCT system to image both the anterior chamber of the eye and the full eye. These methods involve, for example, using long optical delays or dual optical delays, performing numerical resampling, removing mirror-image ambiguity in the digital signal processing of the OCT data, removing mirror-image ambiguity from the OCT data, or unfolding of the aliased component of the image from the OCT data. Each of these methods, however, requires a compromise in either system performance or impacts the system design constraints.

In swept-source OCT (SSOCT), the choice of k-clock period, which corresponds to the sample step size in the optical frequency domain, affects the OCT imaging performance. Generally speaking, for example, imaging across a greater depth in the sample, such as the human eye, requires a higher sampling rate, which corresponds to a finer step size in the optical bandwidth.

Figure 1:
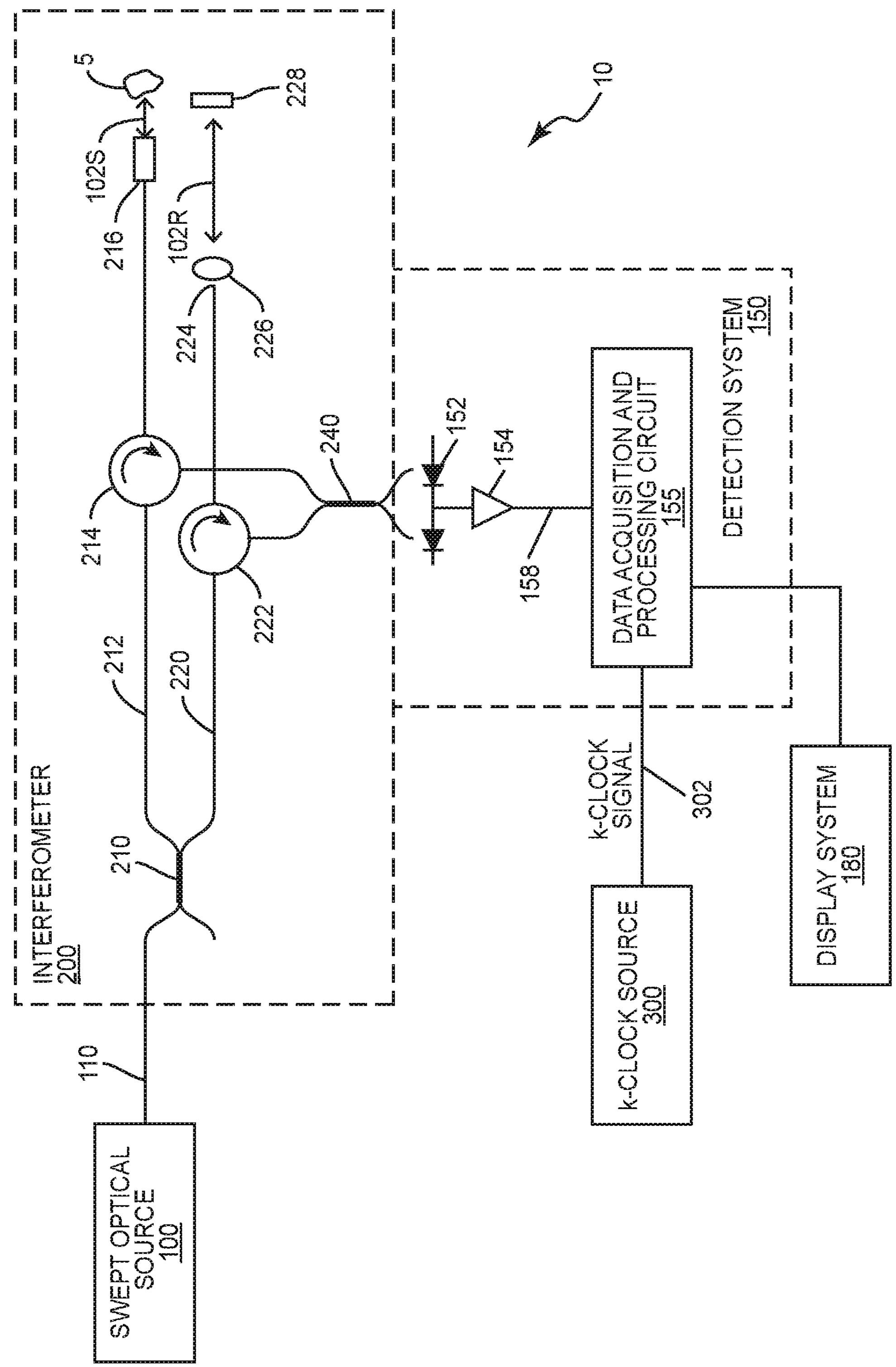
FIG. 1 illustrates components of an example swept-source Optical Coherence Tomography (OCT) system.

To provide context for the detailed description of these techniques that follows, FIG. 1 is first described. FIG. 1 illustrates an example SSOCT system 10, which comprises a swept optical source 100, an interferometer 200, a detection system 150, a k-clock source 300, and a display system 180. It will be appreciated that the details shown here are an example only; other systems may vary in well-known ways.

Swept optical source 100 is typically designed for wavelength tuning, to generate swept optical signals that repeatedly scan over a predetermined optical tuning range, e.g., over an optical wavelength range of 100 nm or greater, at a scanning repetition rate of 1 kilohertz (kHz) or greater. The bandwidth of the optical emission, i.e., the full-width half-maximum (FWHM) bandwidth is typically less than 10 GHz. k-clock source 300 is configured to generate k-clock signals at equally spaced optical frequency sampling intervals, as the output from swept optical source 100 is swept over the source's tuning band. Interferometer 200, in this particular example implemented as a Mach-Zehnder-type interferometer designed for operation at, for example, at optical wavelengths around 1310 nm, is used to analyze the optical signals reflected from the imaged object 5, which may be a human eye. It will be appreciated that interferometer 200 may be based on a different design when designed for different wavelengths.

As seen in the figure, the swept optical output from the swept optical source 100 is coupled to an optical fiber coupler 210 in interferometer, via optical fiber 110. Optical fiber coupler 210 may be a 90/10 optical fiber coupler, for example. The swept optical signal is divided by the coupler 210 between a reference arm 220 and a sample arm 212.

The optical fiber of the reference arm 220 terminates at a fiber end-face 224. The light 102R exiting from the reference arm fiber endface 224 is collimated by a lens 226 and reflected by a mirror 228, in the illustrated implementation. Mirror 228 has an adjustable fiber-to-mirror distance, in one example. This distance determines a reference point in the depth range being imaged, i.e., the position in the sample 5 of the zero-path length difference between the reference arm 220 and the sample arm 212. This distance can be adjusted, in some embodiments, for different sampling probes and/or imaged samples. Light returning from the reference mirror 228 is returned to a reference arm circulator 222 and directed to a 50/50 fiber coupler 240.

The fiber on sample arm 212 terminates at the sample arm probe 216. The exiting swept optical signal 102S is focused by the probe 216 onto the sample 5. Light returning from the sample 5 is returned to a sample arm circulator 214 and directed to the 50/50 fiber coupler 240. The reference arm signal and the sample arm signal are combined in the fiber coupler 240 to generate an optical interference signal.

The optical interference signal is detected and processed in detection system 150. Specifically, in the implementation shown in FIG. 1, a balanced receiver, comprising two optical detectors 152, is located at each of the outputs of the fiber coupler 240. The electronic interference signal from the balanced receiver 152 is amplified by amplifier 154, to produce an interference signal 158 for processing by data acquisition and processing circuit 155A.

Data acquisition and processing circuit 155A of the detection system 150 is used to sample the interference signal output from the amplifier 154. The k-clock signal from the k-clock source 300 is used by the data acquisition circuit 155A to synchronize system data acquisition with the frequency tuning of the optical swept source system 100. Note that because the optical tuning of the optical swept source system 100 may not be linear, with respect to time, the k-clock signal may have irregular periods and thus does not have a fundamental frequency, but rather a frequency range, characterized by an average frequency that may, for the purposes of the present disclosure, be regarded as the k-clock frequency.

Typically, once a complete data set has been collected of the sample 5 by spatially raster-scanning the focused probe beam point over the sample, e.g., in an x-y, fashion or in a theta-z fashion, so that the spectral response at each one of these points is generated from the frequency tuning of the swept optical source 100, the data acquisition and processing circuit 155A performs a Fourier transform on the data, according to well-known techniques, in order to reconstruct the image and perform a 2D or 3D tomographic reconstruction of the sample 5. The information generated by the data acquisition and processing circuit 155A can then be displayed with display system 180, such as a video monitor.

Figure 2:
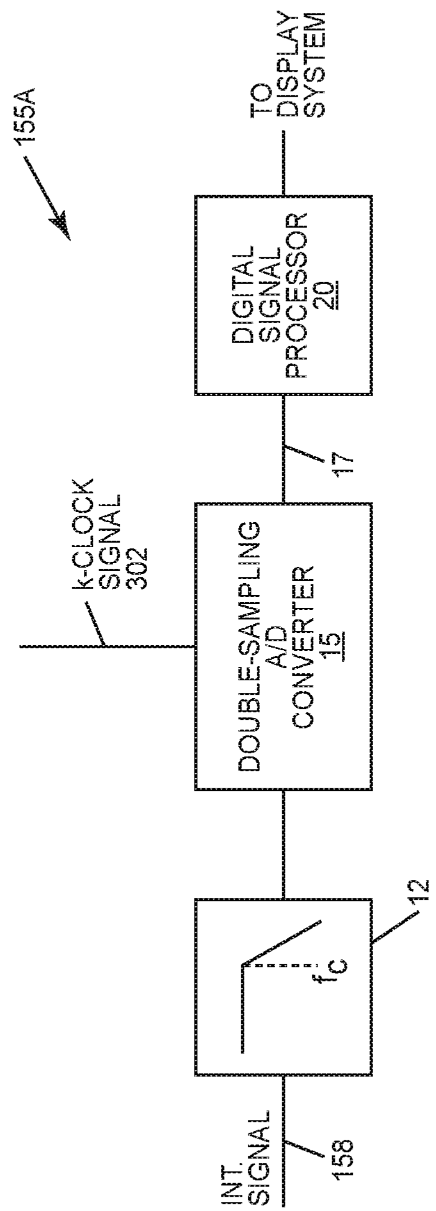
FIG. 2 illustrates components of an example digital acquisition and processing circuit consistent with some embodiments of the presently disclosed invention.

FIG. 2 illustrates further details of an example data acquisition and processing circuit 155A, as might be found in several embodiments of the presently disclosed. As seen in the figure, data acquisition and processing circuit 155A comprises an analog-to-digital (A/D) converter 15, configured to sample interference signal 158 using the k-clock signal 302 as a sampling clock. This produces a sampled OCT signal, on sampling channel 17, which is supplied to a digital signal processor circuit 20 for Fourier processing and image reconstruction.

Before the interference signal 158 is provided to the A/D converter circuit 15, however, it is first filtered by anti-aliasing filter 12. This anti-aliasing filter 12 has a cut-off frequency, $f_c$, with the cut-off frequency being selected to prevent aliasing, which is a well-known phenomenon in digital sampling circuits, arising when the sampled signal includes signal energy at frequencies above one-half the sampling rate of the system. If energy above this Nyquist frequency are present in the input signal, this energy is "folded" onto the lower frequency energy in the sampling process, thus providing a distorted representation of the input signal in the digital samples. To prevent this phenomenon, the cut-off frequency $f_c$ for the anti-aliasing filter is generally selected to be well below one-half the sampling rate, so that any energy above that frequency is sufficiently attenuated by the filter before reaching the A/D converter. It will be appreciated that various specific definitions for a filter's cut-off frequency are used in industry. Accordingly, for the purposes of clarity and definiteness, the term herein is used to refer to the half-power point, i.e., the frequency at which the attenuation of the filter is −3 dB of the filter's nominal passband attenuation.

As noted above, the choice of k-clock period, which corresponds to the sample step size in the optical frequency domain, affects the OCT imaging performance to facilitate the use of OCT for a range of applications, current OCT systems may include a variable-speed k-clock, having a minimum k-clock frequency and a maximum k-clock frequency. However, in these systems, the anti-aliasing filter is designed for the maximum k-clock frequency, $f_{max}$, so that $f_c<f_{max}/2$. As a result, when lower k-clock frequencies are used, e.g., at the lowest k-clock frequency, $f_{min}$, aliasing may occur, i.e., when $f_c>f_{min}/2$, as the anti-aliasing filter will then permit the signal sampled by the A/D circuit to include input frequencies that exceed one-half the sampling rate.

Embodiments of the presently disclosed invention address this problem by sampling the signal provided to the A/D circuit 15 at twice the k-clock frequency, e.g., by sampling at both rising and falling edges of the k-clock. The cut-off frequency $f_c$ for the anti-aliasing filter 12 is selected to have a cut-off frequency that is less than the minimum k-clock frequency $f_{min}$, but the cut-off frequency need not be less than one-half the minimum k-clock frequency $f_{min}$, because of the doubled sampling rate. (The minimum sampling rate, because of the doubled sampling rate, is $2\times f_{min}$) Thus, in practice, the cut-off frequency $f_c$ for the anti-aliasing filter 12 may be greater than one-half the minimum k-clock frequency but less than the minimum k-clock frequency.

With this approach, the full range of k-clock frequencies, with the concomitant tradeoffs in performance, and without aliasing at either extreme. At higher k-clock frequencies, the interference signal is effectively oversampled, as it is sampled at twice the k-clock signal, but this higher sampling rate and signal processing rate is easily accommodated with existing A/D converter circuits and digital signal processing circuits. Decimation of the sampled signal may be utilized, if desired.

Figure 3:
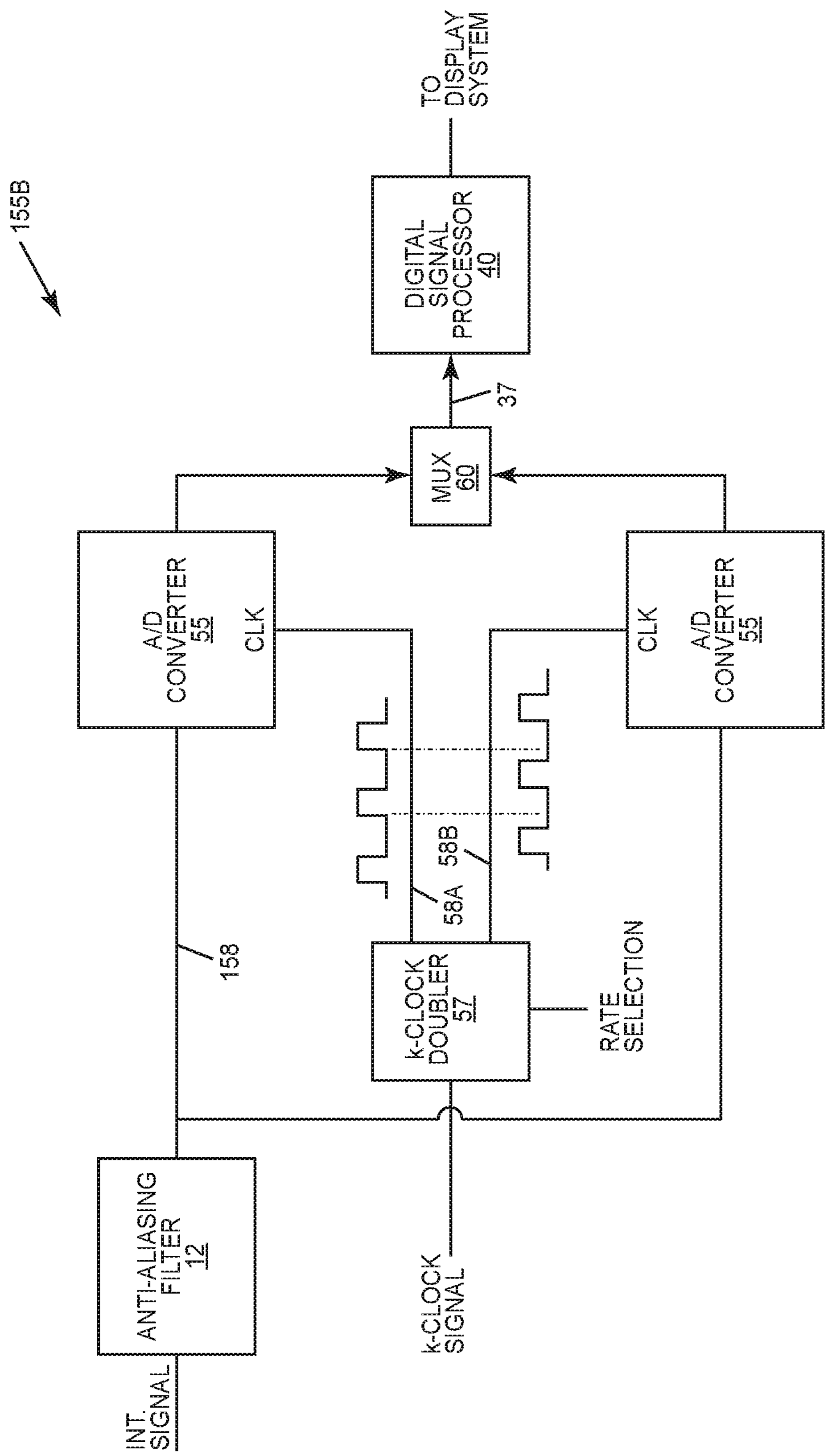
FIG. 3 illustrates components of another example digital acquisition and processing circuit, consistent with other embodiments of the presently disclosed invention.

In the data acquisition and processing circuit illustrated in FIG. 2, A/D converter circuit 15 is configured as a double-sampling A/D converter, e.g., to sample the input signal at both the rising and falling edges of the k-clock signal 302 or, equivalently, at every zero-crossing of the k-clock signal 302. FIG. 3 illustrates another example of a data acquisition and processing circuit 155B, consistent with some embodiments of the presently disclosed invention. As seen in FIG. 3, data acquisition and processing circuit 155B comprises two A/D converters 55, configured in parallel such that each is configured to separately sample the interference signal 158, after sampling by anti-aliasing filter 12. The clock (CLK) inputs to the first and second A/D converters, respectively, are driven by two different replicas of the k-clock signal, shown in the figure as clock signals 58A and 58B, respectively, with one clock signal (58B) being phase-shifted, i.e., delayed, with respect to the other (58A). In the illustrated example, this phase shift is approximately 180 degrees, although different phase shifts may be employed, e.g., to provide a uniform sampling interval in the k-domain. The first and second k-clock signals 58A and 58B are generated in the circuit shown in FIG. 3 by k-clock doubler circuit 57. The outputs of the first and second A/D converters 55 are combined, with a multiplexer (MUX) 60, to produce a sampled OCT interference signal supplied to digital signal processor circuit 40 via sampling channel 37. As was the case in the circuit shown in FIG. 3, digital signal processing circuit 40 performs Fourier processing and image reconstruction based on the sampled OCT interference signal provided to it via sampling channel 37, again using well-known techniques, to selectively produce half-depth OCT images or full-depth OCT images, corresponding to the half-rate and full-rate modes, respectively.

FIGS. 2 and 3, as described above, illustrate specific examples of OCT data acquisition and processing circuits for use in producing an OCT image based on a swept-source OCT interference signal. These and variations of these may be used, for example, in SSOCT systems like the one illustrated in FIG. 1, but may of course be used in systems having varying designs and configurations. The illustrated circuits are thus specific examples of an OCT data acquisition and processing circuit that includes a k-clock circuit configured to selectively output a k-clock signal at any of a plurality of k-clock frequencies ranging from a minimum k-clock frequency to a maximum k-clock frequency, an anti-aliasing filter configured to filter the swept-source OCT interference signal, to produce a filtered OCT interference signal, where the anti-aliasing filter has a cut-off frequency greater than one-half the minimum k-clock frequency but less than the minimum k-clock frequency, and an A/D converter circuit coupled configured to sample the filtered OCT interference signal at twice the k-clock frequency, to produce a sampled OCT interference signal.

It will be appreciated that in some embodiments of the data acquisition and processing circuits as disclosed herein, the A/D converter circuit is configured to sample the filtered OCT interference signal on every rising edge and every falling edge of the k-clock signal. In other embodiments, the A/D converter circuit comprises first and second A/D converters, the first A/D converter being configured to sample the filtered OCT interference signal at the k-clock frequency, using the k-clock signal, and the second A/D converter being configured to separately sample the filtered OCT interference signal at the k-clock frequency, using a phase-shifted replica of the k-clock signal. In these latter embodiments, the A/D converter circuit further comprises a multiplexer to combine the sampled outputs from the first and second A/D converters to obtain the sampled OCT interference signal.

In some embodiments, an OCT system including an OCT data acquisition and processing circuit as disclosed herein may further include a swept optical source and an interferometer coupled to an output of the swept optical source, the interferometer in turn comprising a detector circuit configured to generate the swept-source OCT interference signal from an optical interference signal produced by the interferometer. In some embodiments, an OCT system including an OCT data acquisition and processing circuit as disclosed herein may further include a digital signal processing circuit configured to process the sampled OCT interference signal to obtain an OCT image, and a display configured to display the OCT image.

The specific embodiments described above illustrate but do not limit the invention. It should also be understood that numerous modifications and variations are possible in accordance with the principles of the present invention, as described above and as claimed below.

What is claimed is:

1. An Optical Coherence Tomography (OCT) data acquisition and processing circuit for use in producing an OCT image based on a swept-source OCT interference signal, the OCT data acquisition and processing circuit comprising:

a k-clock configured to selectively output a k-clock signal at any of a plurality of k-clock frequencies ranging from a minimum k-clock frequency to a maximum k-clock frequency;

an anti-aliasing filter configured to filter the swept-source OCT interference signal, to produce a filtered OCT interference signal, the anti-aliasing filter having a cut-off frequency greater than one-half the minimum k-clock frequency but less than the minimum k-clock frequency; and an analog-to-digital (A/D) converter circuit coupled to an output of the anti-aliasing filter and configured to sample the filtered OCT interference signal at twice the k-clock frequency, to produce a sampled OCT interference signal;

wherein the A/D converter circuit comprises first and second A/D converters, the first A/D converter being configured to sample the filtered OCT interference signal at the k-clock frequency, using the k-clock signal, and the second A/D converter being configured to separately sample the filtered OCT interference signal at the k-clock frequency, using a phase-shifted replica of the k-clock signal, the A/D converter circuit further comprising a multiplexer to combine the sampled outputs from the first and second A/D converters to obtain the sampled OCT interference signal.

2. An OCT system comprising the OCT data acquisition and processing circuit of claim 1, and further comprising:

a swept optical source; and an interferometer coupled to an output of the swept optical source, the interferometer comprising a detector circuit configured to generate the swept-source OCT interference signal from an optical interference signal produced by the interferometer.

3. An OCT system comprising the OCT data acquisition and processing circuit of claim 1, and further comprising:

a digital signal processing circuit configured to process the sampled OCT interference signal to obtain an OCT image; and a display configured to display the OCT image.

4. The OCT data acquisition and processing circuit of claim 1, further comprising:

a k-clock doubler configured to produce the phase-shifted replica of the k-clock signal.

5. An Optical Coherence Tomography (OCT) data acquisition and processing circuit comprising:

a k-clock configured to selectively output a k-clock signal at any of a plurality of k-clock frequencies ranging from a minimum k-clock frequency to a maximum k-clock frequency;

a k-clock doubler configured to produce a phase-shifted replica of the k-clock signal;

an anti-aliasing filter configured to filter the swept-source OCT interference signal, to produce a filtered OCT interference signal, the anti-aliasing filter having a cut-off frequency greater than one-half the minimum k-clock frequency but less than the minimum k-clock frequency;

first and second A/D converters, the first A/D converter being configured to sample the filtered OCT interference signal at the k-clock frequency, using the k-clock signal, and the second A/D converter being configured to separately sample the filtered OCT interference signal at the k-clock frequency, using the phase-shifted replica of the k-clock signal, the A/D converter circuit further comprising a multiplexer to combine the sampled outputs from the first and second A/D converters to obtain the sampled OCT interference signal;

a digital signal processor, an input of the digital signal processor coupled to an output of the analog-to-digital (A/D) converter circuit;

the multiplexer coupled to an output of the first A/D converter and to an output of the second A/D converter; and the digital signal processor coupled to an output of the multiplexer.

6. An OCT system comprising the OCT data acquisition and processing circuit of claim 5, and further comprising:

a swept optical source; and an interferometer coupled to an output of the swept optical source, the interferometer comprising a detector circuit configured to generate the swept-source OCT interference signal from an optical interference signal produced by the interferometer.

7. An OCT system comprising the OCT data acquisition and processing circuit of claim 5, and further comprising:

a digital signal processing circuit configured to process the sampled OCT interference signal to obtain an OCT image; and a display configured to display the OCT image.

* * * * *